United States Patent [19]

Bjorkholm

[11] Patent Number: 4,768,214
[45] Date of Patent: Aug. 30, 1988

[54] IMAGING

[75] Inventor: Paul J. Bjorkholm, Sharon, Mass.

[73] Assignee: American Science and Engineering, Inc., Cambridge, Mass.

[21] Appl. No.: 853,368

[22] Filed: Apr. 15, 1986

Related U.S. Application Data

[63] Continuation of Ser. No. 691,737, Jan. 16, 1985, abandoned, which is a continuation of Ser. No. 426,380, Sep. 29, 1982, abandoned.

[51] Int. Cl.4 .......................................... G01N 23/201
[52] U.S. Cl. ...................................... 378/87; 378/146
[58] Field of Search ........................................ 378/5-7, 378/87, 146, 901; 364/414

[56] References Cited

U.S. PATENT DOCUMENTS

| | | |
|---|---|---|
| Re. 28,544 | 9/1975 | Stein et al. . |
| 2,966,587 | 12/1960 | Faulkner, Jr. et al. . |
| 2,977,478 | 3/1961 | Wuppermann . |
| 3,188,471 | 6/1965 | Hansen et el. . |
| 3,210,545 | 10/1965 | Barnett . |
| 3,569,708 | 3/1971 | Weinbaum et al. . |
| 3,809,904 | 5/1974 | Clarke et al. . |
| 3,884,816 | 5/1975 | Takahashi ............................. 378/99 |
| 3,927,318 | 12/1975 | Macovski . |
| 3,936,638 | 2/1976 | Gibbons ................................. 378/5 |
| 3,937,965 | 2/1976 | Vasseur ................................. 378/7 |
| 3,961,186 | 6/1976 | Leunbach . |
| 3,965,353 | 6/1976 | Macovski . |
| 4,047,029 | 9/1977 | Allport . |
| 4,123,654 | 10/1978 | Reiss et al. . |
| 4,132,895 | 1/1979 | Froggatt ................................. 378/7 |
| 4,147,931 | 4/1979 | Puumalainen . |
| 4,228,351 | 10/1980 | Snow et al. . |
| 4,342,916 | 8/1982 | Jatteau ..................................... 378/6 |
| 4,384,209 | 5/1983 | Wagner et al. . |
| 4,529,882 | 7/1985 | Lee ................................... 250/363 S |
| 4,549,307 | 10/1985 | Mucovski . |

OTHER PUBLICATIONS

"Computerized Tomography: Taking Sectional X-rays", by Swindell et al., Physics Today 12-1977.
"Flying Spot X-Ray Imaging System", by Stein et al., Materials Evaluation, Jul. 1972, vol. 30, #7.
Kaufman, "Measurement of Absolute Lung Density by Compton-Scatter Densitometry", IEEE Transactions on Nuclear Science, vol. NS-23, No. 1, Feb. 1976, pp. 599-605.

Primary Examiner—Craig E. Church
Assistant Examiner—John C. Freeman
Attorney, Agent, or Firm—Pollock, Vand Sande & Priddy

[57] ABSTRACT

Method and apparatus for imaging using penetrating radiant energy provides a resulting image with elements of intensity related to atomic number. A penetrating radiant energy source is used for generating a flying spot. A first detector is located to be responsive to transmitted energy, e.g. the flying spot traverses the first detector. A second detector is located substantially coplanar with the first detector to be responsive to scattered energy, as the flying spot scans a target. The signals produced by the first and second detectors are combined to produce an image array having elements of intensity related to atomic number. A method and apparatus for non-invasively measuring density using the apparatus already recited, is also disclosed.

19 Claims, 3 Drawing Sheets

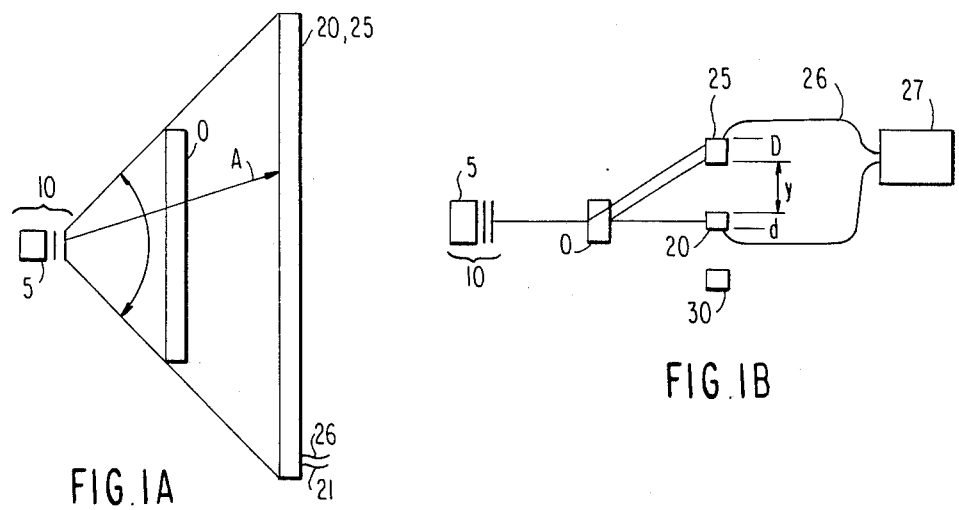
FIG.1A
FIG.1B
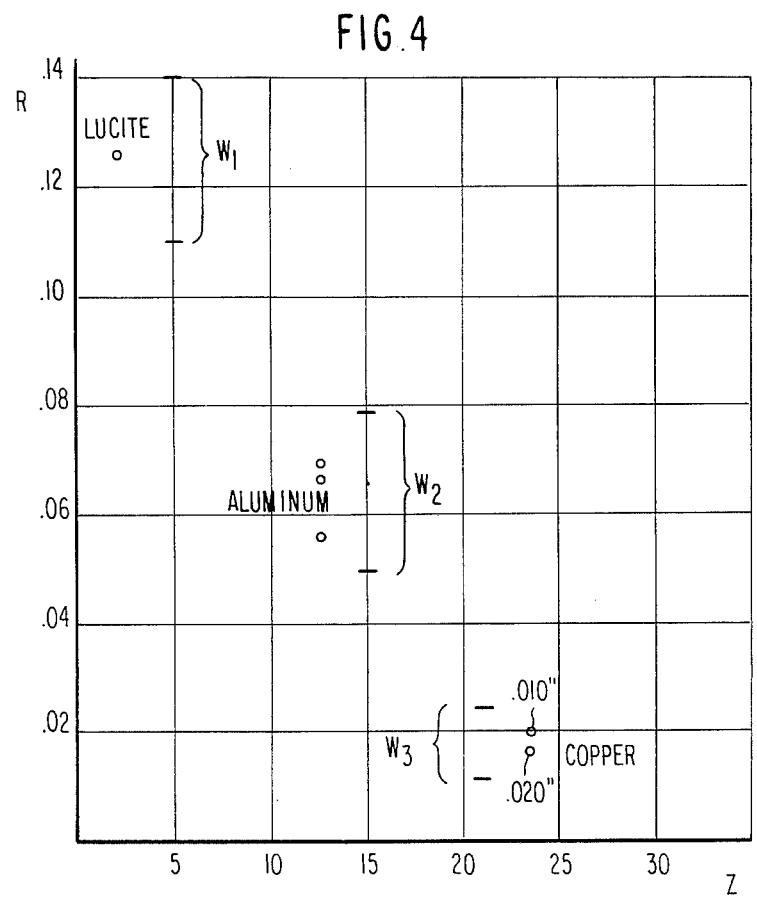
FIG.4

IMAGING

This is a continuation of co-pending application Ser. No. 691,737, filed on Jan. 16, 1985, and abandoned Apr. 15, 1986, which is a continuation of co-pending application Ser. No. 426,380, filed on Sept. 29, 1982, now abandoned.

DESCRIPTION

1. Field of the Invention

The present invention relates to imaging using penetrating radiant energy, and more particularly to x-ray imaging.

2. Background Art

The use of penetrating radiant energy as an imaging technique has been available in the prior art for many years. Typically, such an imaging system includes three components, a source of appropriate penetrating radiant energy, a detector which is responsive to the radiant energy reaching the detector, and an imaging device for producing an image which is created in dependence on the signals produced by the detector. In the earliest forms, the detector and imaging device were united in the form of a coated film. Typically, an object to be imaged, for example a human being, was located between a source of penetrating radiant energy, such as an x-ray source, and the detector, i.e. the film. After a suitable period of illumination, the film was developed to produce an image which was useful in various medical diagnoses.

Although in use for quite some time, the technique has many drawbacks. Since the image is developed on a single plane it is difficult to obtain a good spatial concept of the object being imaged. Information respecting density and thickness is mixed since both parameters produce an identical effect, i.e. stopping more or less of the penetrating radiant energy.

Improvements have of course been made, and while the following portions of the application discuss some of those improvements and the present invention as specific to x-ray illumination, it should be apparent that other forms of penetrating radiant energy have also been employed and can be employed as an illumination source in accordance with the invention. Those improvements have included detectors capable of selectively responding to different energy levels, and capable of providing increased resolution when used together with, for example, apparatus producing a flying spot of penetrating radiant energy rather than fan beams (line illumination) or even area illumination.

The relatively new field of computer tomography has added the power of the computer to the imaging function. This technique allows the object to be illuminated and the detector response captured, from a plurality of different directions. Once this is accomplished, the computer processes information captured in the detector response as a function of direction of illumination to produce a cross-sectional image which provides a vastly improved spatial concept of the object being imaged.

Another capability provided by the computer is the ability to produce an enhanced image. The typical display medium used in computer tomography and other penetrating radiant energy imaging apparatus is the cathode ray tube. The cathode ray tube image has a finite contrast range. However, the entire contrast range of the cathode ray tube can be used to display only a portion of the contrast range available in the captured information. Of course, portions of the image whose contrast lies outside the range being used cannot be seen; however, those portions of the image whose contrast lies within the range are greatly enhanced. The two parameters associated with this technique are called the window and level. The level determines the mid-point of the contrast range which will be displayed and the window describes the total contrast range which will be displayed. Notwithstanding these advances, there still remains problems for which the prior art provides no solution. The particular problems which this invention addresses relates to the fact that most of the objects being imaged are complex, i.e. made up of aggregations of different elements, compounds, tissues or the like. The unsolved problem is the production of an image showing some, but not all of the components of the object, i.e. to isolate one or a few components for imaging.

One prior art technique aimed at this problem is imaging using three nearly monochromatic but different illumination energies. For example, in imaging a human, the illumination is chosen as one below the k-edge of iodine, and two above it. Three different time sequential images are taken, and are then combined so that only the image of the iodine component remains, the bone and soft tissue cancel out. Mistretta has shown that this is a viable technique. However, the filtering required to produce the monochromatic illumination severely reduces the available energy intensity such that the results are photon limited.

It is well known that the mass attenuation coefficients depend on both atomic number and energy. The photo electric and Compton components are different functions of energy. Brody et al pointed out that if you could take two images at different energies, you can combine the images in such a way that the contribution to the image from mass of a single atomic number can be removed. Thus, an image can be created which has no contribution from a component with the single atomic number. In the course of this work, Brody illustrated the use of two polychromatic energy spectra, even through there is some overlap. For purposes of this discussion, we shall use the term primary image or primary images to refer to the data collected by illuminating an object and the image that is or could be produced thereby, either directly or by selection of window and level parameters. There exists a set of primary images that can be generated from such data, a first image by displaying the raw data and others that can be produced by various windows and levels. A secondary image, such as that proposed by Brody, is an image created by combining two or more primary images.

Both of these prior art techniques, however, suffer from a common failing, and that is that they use a common source and detector, and thus the different primary images that are obtained (which are later manipulated to obtain secondary images) are necessarily obtained at different times, i.e. the different primary images are time sequentially generated. To the extent that there is any movement in the object being imaged then, the secondary images obtained as a result of manipulating the primary images are inaccurate.

Another failing of the Brody technique is that the secondary image he creates is capable of eliminating image contributions from mass of a single atomic number. To eliminate image contributions from mass of a different atomic number, a different secondary image must be created. While this does not require re-imaging the target (or patient), it does require additional processing. The further function of producing an image which is composed solely of contributions from mass of a chosen atomic number is not addressed in the prior art.

It is therefore one object of the invention to provide a method and apparatus for selectively imaging in which at least two different primary images are obtained which can then be later combined or processed to produce a secondary image, but in which all the primary images are simultaneously obtained. It is another object of the invention to provide an imaging technique allowing isolation of a single component of a complex object which does not require monochromatic or nearly monochromatic illumination, and thus is not energy intensity or photon limited. It is still another object of the invention to provide a method and apparatus for isolating a selected component of a complex object to be imaged which employs a single illumination source, which does not limit the spectrum of that souce (and which thus overcomes the energy intensity limintations of monochromatic techniques and apparatus), but which instead employs two different detectors, a first detector arranged to be responsive to a transmitted ray, and a second detector arranged to be responsive to a scattered ray. It can be shown (see below) that an appropriate second image (which is a combination of two primary images, one obtained from transmitted energy and the other obtained from scattered energy) can be manipulated to enhance one component (based on atomic number) at the expense of all others, and the particular component being enhanced can be chosen after the primary images are obtained and after the secondary image is obtained.

It is therefore another object of the invention to obtain two primary images from a single illumination, one from transmitted energy and the other from scattered energy; and then combine them to obtain a secondary image which is not a function of mass density ($\rho$) or thickness ($l$).

Those skilled in the art are aware that typical projection radiographic images mix thickness and density information and many times it is important to unscramble the mixed information. It is another object of the invention to provide for processing of the scattered and transmitted images to produce a secondary image. Selecting window and level parameters allows the viewer to focus in on an atomic number plane which is not contaminated with density or thickness data. That is, by varying window and level, the viewer can enhance image contributions from particular components of the target with similar atomic number.

The ability to isolate image components in terms of atomic number can also be applied to non-invasive measuring of mass density. It is therefore another object of the invention to provide a method and apparatus for the non-invasive quantitative evaluation of mass density of selected target components such as bone.

SUMMARY OF THE INVENTION

Accordingly, these and other objects of the invention are met in an apparatus useful in selectively imaging using penetrating radiant energy. That apparatus includes a source of penetrating radiant energy; an x-ray source is one example. Adjacent the source of penetrating radiant energy is an apparatus for directing the energy toward a target area; a collimator may be used, and in a preferred embodiment, this apparatus is represented by a scanning device to shape the emitted x-radiation into a scanning beam which repeatedly scans the target area in a raster scan fashion. Finally, a radiant energy detecting arrangement is employed which includes a first radiant energy detector located to be responsive to the radiant energy passing directly through an object (transmitted) located in the target area, and a second radiant energy detector located to be responsive to radiant energy scattered by an object located in the target area.

As will be described hereinafter, the desired image is produced by first storing signals produced by the first and second radiant energy detectors in such a way that signals from the first and second radiant energy detectors each form an array, and the desired array is provided by selectively combining the arrays produced by the first and second radiant energy detectors.

Thus, the first radiant energy detector produces a time sequence of signals which are sampled, A/D converted and stored in an array to form a first primary array T. The second radiant energy detector produces (simultaneously) a time sequence of signals which are sampled, A/D converted and stored in a different array to form a second primary array S. For each element $T_{i,j}$ and $S_{i,j}$, of arrays T and S, an element $R_{i,j}$ of a secondary array R is formed. The secondary array R will allow production of an image in which image components can be enhanced based on atomic number.

Therefore, in one aspect the invention provides a projection radiographic apparatus useful in selectively imaging an object using penetrating radiant energy comprising:

source means for emitting penetrating radiant energy;

means for directing said penetrating radiant energy emitted by said source means towards a target area;

first radiant energy detecting means located to be responsive to said radiant energy passing directly through an object located in said target area; and second radiant energy detecting means located to be responsive to said radiant energy scattered by an object located in said target area.

In another aspect, the invention allows measurements of internal components of a target in a non-invasive manner. In addition to isolating, in an image, components of the target with atomic number in the vicinity of a selected quantity, density measurements can be made, non-invasively. One particular utility of this technique is measurement of bone mineral density without surgery. As will be shown below, the direct and scattered image arrays can be used, with easily obtained supplemental data, to evaluate bone density. Application of the invention to measurement of bone density is but one example and other applications will occur to those skilled in the art after reviewing the description.

In illuminating the target, care is taken to illuminate the target in at least two different swaths, a first including, in its line of sight, the internal component whose density is to be measured, and at least another swath with a line of sight excluding the internal component. After illuminating, scattered and transmitted image arrays are stored as described above. In addition to the data contained in the transmitted and scattered image arrays, computation of the internal component's density requires the thickness of the target, and the thickness of the internal component. Of course, the target thickness can readily be measured with conventional techniques. Thickness of the internal component can be easily measured using a projection radiograph. It is then only necessary to identify to the machine storing the scattered and transmitted image arrays, two regions of interest or swaths, one excluding the internal component whose density is to be measured, and the other including the internal component whose density is to be measured.

Density can then be computed using the expression:

$$\frac{[S_{i,b}/T_{i,b} - S_{i,a}/T_{i,a}(1 - t_B/t_T)]}{\sigma_{KN} t_B} \quad (1)$$

In this expression, the subscripts i,b and i,a identify respectively, the two different swaths or regions of interest; i,b identifying the swath including the internal component, and i,a identifying the swath excluding the internal component. The transmitted and scattered image arrays are identified by T and S, respectively. The thickness of the object is identified as $t_T$ and the thickness of the internal component is identified as $t_B$. Finally, the parameter $\sigma_{KN}$ is the Klein Nishina cross-section for a free electron (a function of illuminating energy only).

Accordingly, in respect of this aspect, the invention provides a method of remote measurement of density of a component of a complex target in which said component is entirely submerged in another component of said complex target, said method comprising the steps of:

measuring thickness of a selected section of said complex object and thickness of said component at said section;

illuminating said section of said complex object in at least two swaths with a sweeping beam of radiant energy directed approximately perpendicular to said selected section while slowly indexing said target relative to said sweeping beam so that said first swath has a line of sight excluding said component and said second swath has a line of sight including said component;

simultaneously detecting transmitted and scattered radiant energy from said target;

sampling and storing said detected transmitted and scattered radiant energy in a pair of ordered arrays T and S, respectively; and computing:

$$\frac{[S_{i,b}/T_{i,b} - S_{i,a}/T_{i,a}(1 - t_B/t_T)]}{\sigma_{KN} t_B} \quad (2)$$

where the subscripts i,b and i,a identify said second and first swaths, respectively, $t_B$ is said measured thickness of said component at said section, $t_T$ is said measured thickness of said selected section of said complex object and $\sigma_{KN}$ is the Klein Nishina cross-section for a free electron.

BRIEF DESCRIPTION OF THE DRAWINGS

The present invention will now be further described to enable those skilled in the art to make and use the invention in the following portions of this specification when taken in conjunction with the attached drawings in which like reference characters identify identical apparatus, and in which:

FIGS. 1A and 1B are plan and elevation views of a representative embodiment of the invention;

FIG. 4 is a plot of R vs. Z for targets of varying Z and thickness;

DETAILED DESCRIPTION OF PREFERRED EMBODIMENT

Figure 2:
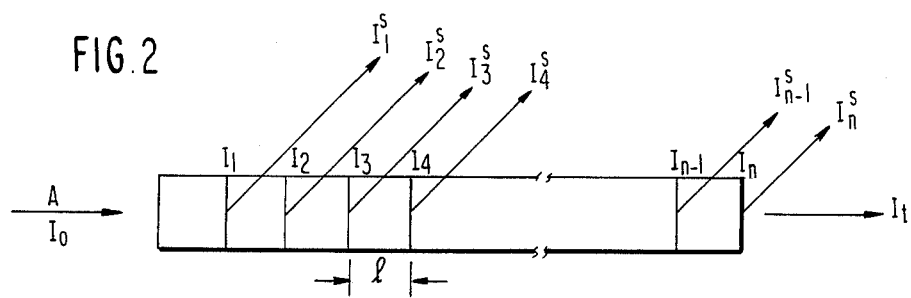
FIG. 2 is useful in describing the theoretical basis for the invention, and relating the direct and scattered rays, which are detected by the described detectors, and the relationship of the intensities those rays bear to the image desired to be produced.

FIGS. 1A and 1B illustrate, in block schematic fashion, plan and elevation views of a preferred embodiment of the invention. As shown in FIGS. 1A and 1B, a source of x-radiation 5 is located so as to emit radiation in the direction of a target area; in FIGS. 1A and 1B the target area is indicated by the position of the object O which is located in the target area. Associated with the x-ray source 5 is a device for directing the x-radiation toward the target area. In a preferred embodiment, that includes apparatus for forming a scanning spot beam of x-radiation. As best seen in FIG. 1A, the scanning spot beam repeatedly traverses a region in space occupied by detectors 20, 25, and at an arbitrary instant in time the spot beam may follow the direction of the arrow A. Since those skilled in the art are aware of a variety of devices for producing scanning spot beams to traverse specified regions in space, that apparatus will not be described in detail herein; however, reference is made to U.S. Pat. Nos. 4,031,401, Re. 28,544, 3,790,799, 4,242,593 and 4,260,898.

As best seen in FIG. 1B, the typical spot beam A is directed into the target area, in which the object O lies. Located on the other side of the object O from the x-ray source 5, is the detector region, and as shown in FIG. 1B, the detector region is occupied by at least two different x-ray detectors. A first detector 20 is located so as to intercept radiant energy passing directly through the object O. On the other hand, a second detector 25, located on the same side of the object O as is the detector 20, but the second detector 25 is located so as to intercept forward scattered radiant energy from an object located in the target area, that is radiant energy scattered at an acute angle (see FIG. 1B) from the object located in the target area.

The construction of each of the detectors 20 and 25 can follow prior art techniques; what is important is that the detectors be located so as to selectively intercept either direct or scattered radiation, and to separately develop corresponding electrical signals on output conductors 21 and 26, representative of direct and scattered radiation, respectively. However the detectors are preferably coplanar as shown in FIGS. 1A and 1B. As shown in FIG. 1B, the detector 20 has a height d (perpendicular to the direction of the transmitted ray A), whereas the detector 25 has a height D (measured in the same direction), and the detector 25 is spaced a distance y (again measured perpendicular to the direction of the transmitted ray A) from the uppermost portion of the detector 20. The particular dimensions d, D and y will be selected by those skilled in the art based on the criteria that the detector 20 is to intercept transmitted radiation, whereas detector 25 is to intercept only or mostly forward scattered radiation. Based on this criteria, FIG.

1B shows an additional optional detector 30 which may form part of the second detector, i.e. to intercept forward scattered radiation. Furthermore, the second detector 25 and 30 may in practice cover a substantial area, rather than being a line detector, as is the detector 20. That is, the second detector may occupy a substantial region in a plane perpendicular to the direct ray A, except of course in the region occupied by the first detector 20. With the geometry as described in FIGS. 1A and 1B then, the desired image is constructed from signals produced by two detectors, a first detector 20 arranged to be responsive to a direct ray, and a second detector 25 arranged to be responsive to a forward scattered ray. As the scanning spot beam scans the object in a plane defined by the scanning spot beam, the signals produced by the first and second detectors 20 and 25 are stored, i.e. the outputs of the first and second detectors are subjected to a sampling and analog-to-digital conversion process, whereafter the signals are separately stored in first and second image arrays. The device 27 is responsive to signals on conductors 21 and 26 for simulaneously sampling, digitizing and storing said signals in T and S ordered arrays. In addition, and as will be described hereinafter, the device 27 provides for combining the T and S ordered arrays to produce a secondary image array R. Finally, the device 27 provides for producing an image of the secondary array R using selectable window and level parameters. The device 27 can be implemented with conventional devices including minicomputers and/or microprocessors and associated CRT's. Accordingly, further description of the device 27 is not required.

As thus far described, the signals produced by the first and second detectors are limited to producing line images representing the line of the object O scanned by the spot beam A. As is typical, however, of the use of scanning spot beams, a raster sweep action is produced by slowly (relative to the speed of the scanning) and relatively translating the object O in a direction perpendicular to the plane of the scanning spot beam. That is, the translation can be produced by motion of the object O (with source and detectors fixed) or motion of source and detectors (with the object fixed). For each one or several sweeps of the spot beam, the source/detector or object is indexed perpendicular to the plane of the spot beam so that on following sweeps, a different region (or a line) of the object is scanned by the scanning of the spot beam.

The prior art to the invention proceeds by noting the attenuation coefficient $\mu_t$ is a function of Z (atomic number) and E (illumination energy). It has been shown:

$$\mu_t(Z,E) = a_c(Z)\mu_c(E) + a_p(Z)\mu_p(E) \qquad (3)$$

where the subscripts c and p relate to Compton scattering and photo electric attenuation, the coefficients, a, are functions of Z, only.

For any line of sight and energy $E_1$:

$$I_t = I_0 e^{-\int \mu(Z,E_1)\rho dy} \qquad (4)$$

where:
$I_t$ is the transmitted energy (incident on a detector) and
$I_0$ is the energy incident on the object,
and the integral is along a line of sight from source to the detector.

We define:

$$S_1 \equiv -\ln(I_t/I_0) = \int \mu(Z,E_1)\rho dy \qquad (5)$$

$$= \mu_c(E_1)\int a_c(Z)\rho dy + \mu_p(E_1)\int a_p(Z)\rho dy \qquad (6)$$

After imaging at energy $E_1$, the prior art re-images at energy $E_2$, to define:

$$S_2 = \mu_c(E_2)\int a_c(Z)\rho dy + \mu_p(E_2)\int a_p(Z)\rho dy \qquad (7)$$

and determines b, such that $$S_1 + bS_2 = 0 \qquad (8)$$

or $$b = -S_1/S_2 = \frac{-\mu_c(E_1)\int a_c(Z)\rho dy - \mu_p(E_1)\int a_p(Z)\rho dy}{\mu_c(E_2)\int a_c(Z)\rho dy + \mu_p(E_2)\int a_p(Z)\rho dy} \qquad (9)$$

If such a combination image is formed, then lines of sight with Z satisfying the equation will disappear from the combined image, other lines or sight will remain. If Z is constant over the integral we can say:

$$b = \frac{-\mu_c(E_1)a_c(Z) - \mu_p(E_1)a_p(Z)}{\mu_c(E_2)a_c(Z) + \mu_p(E_2)a_p(Z)} \qquad (10)$$

So long as $$\frac{\mu_p(E_1)}{\mu_c(E_1)} \neq \frac{\mu_p(E_2)}{\mu_c(E_2)} \qquad (11)$$

which in general is true, b will be a function of Z.

Note this requires two different illuminations, one with energy $E_1$, the other at $E_2$. Furthermore, while this prior art allows elimination of the contributions in an image from mass of a particular atomic number, the problem of isolating, in an image, contribution from mass of a particular atomic number is not addressed.

We now refer to FIG. 2 to describe how the image arrays produced by the first and second detectors of the invention can be manipulated to isolate a particular element, compound, tissue, etc. This isolation is, as will be described hereinafter, based on atomic number Z.

FIG. 2 shows a cross-section of the object O located in the target area on which is incident the spot beam A with intensity $I_0$. The direct ray transmitted through the object O has an intensity $I_t$. For convenience, the object O is (conceptually) sub-divided into a sequence of elemental regions each of length l in the direction of the ray A. The boundary of each region is numbered, and since there are n regions, there are n interfaces. In general, $I_x$ is the intensity of the direct ray crossing the boundary x, and the scattered ray $I_x^s$ is the radiation scattered by the region x; since there are n regions, x can take on any integer value between 1 and n. Finally, since we have postulated that each of the elemental regions is of a width l, then $nl = t$, where t is the thickness (in the direction of the ray A) of the object O.

We can then relate:

$$I_1 = I_0 e^{-\mu_t \rho l} \qquad (12)$$

where
$\mu_t$ = total mass attenuation coefficient,
$\rho$ = mass density,
l = elemental thickness.

$$I_1{}^s \alpha (I_0 - I_0 e^{-\mu_c \rho l}) e^{-\mu_t \rho (t - l/2)} \tag{13}$$

where $\mu_c$ = Compton scattering coefficient,
$t = nl$ = total thickness.

This can be reduced to:

$$I_0(1 - e^{-\mu_c \rho l}) e^{-\mu_t \rho (t - l/2)} \tag{14}$$

and $$I_2 = I_1 e^{-\mu_t \rho l} = I_0 e^{-\mu_t \rho 2l} \tag{15}$$

$$I_2{}^s \alpha (I_1 - I_1 e^{-\mu_c \rho l}) e^{-\mu_t \rho (t - 3l/2)} \tag{16}$$

$$\alpha I_0 e^{-\mu_t \rho l} (1 - e^{-\mu_c \rho l}) e^{-\mu_t \rho (t - 3l/2)} \tag{17}$$

$$\alpha I_0 (1 - e^{-\mu_c \rho l}) e^{-\mu_t \rho (t - l/2)} \tag{18}$$

and finally $$I_n = I_0 e^{-\mu_t \rho n l} = I_t \tag{19}$$

$$I_n{}^s \alpha I_0 (1 - e^{-\mu_c \rho l}) e^{-\mu_t \rho (t - l/2)} \tag{20}$$

The scattered radiation, for the entire thickness t $$I_s \propto \sum_{i=1}^{n} I_i{}^s = n I_0 (1 - e^{-\mu_c \rho l}) e^{-\mu_t \rho (t - l/2)} \tag{21}$$

Now we let $l \to 0$, maintaining $nl = t$.

$$I_t = I_0 e^{-\mu_t \rho t} \tag{22}$$

and $I_s$ (the scattered radiation):

$$I_s \alpha n I_0 (\mu_c \rho l - \tfrac{1}{2} \mu_c{}^2 \rho^2 l^2 + \ldots) e^{-\mu_t \rho t} \tag{23}$$

$$\alpha \mu_c \rho t I_0 e^{-\mu_t \rho t} \tag{24}$$

Alternatively:

$$I_t = I_0 e^{-\int \mu_t \rho \, dy} \tag{25}$$

$$I_s \alpha \int \mu_c \rho \, dy \, I_0 e^{-\int \mu_t \rho \, dy} \tag{26}$$

We then define:

$$R \propto \frac{I_s/I_t}{-\ln(I_t/I_0)} = \frac{\int \mu_c \rho \, dy}{\int \mu_t \rho \, dy} \tag{27}$$

If Z is constant along the direct path between source and detector, then:

$$R \propto \frac{\mu_c}{\mu_t} \tag{28}$$

and is a unique function of Z.

However, we know $I_s$ and $I_t$, these are what the detectors see, and thus our primary images T and S are made up of sampled and digitized versions of $I_s$ and $I_t$. So we can compute R for our image, point by point, using equation 27.

Figure 3:
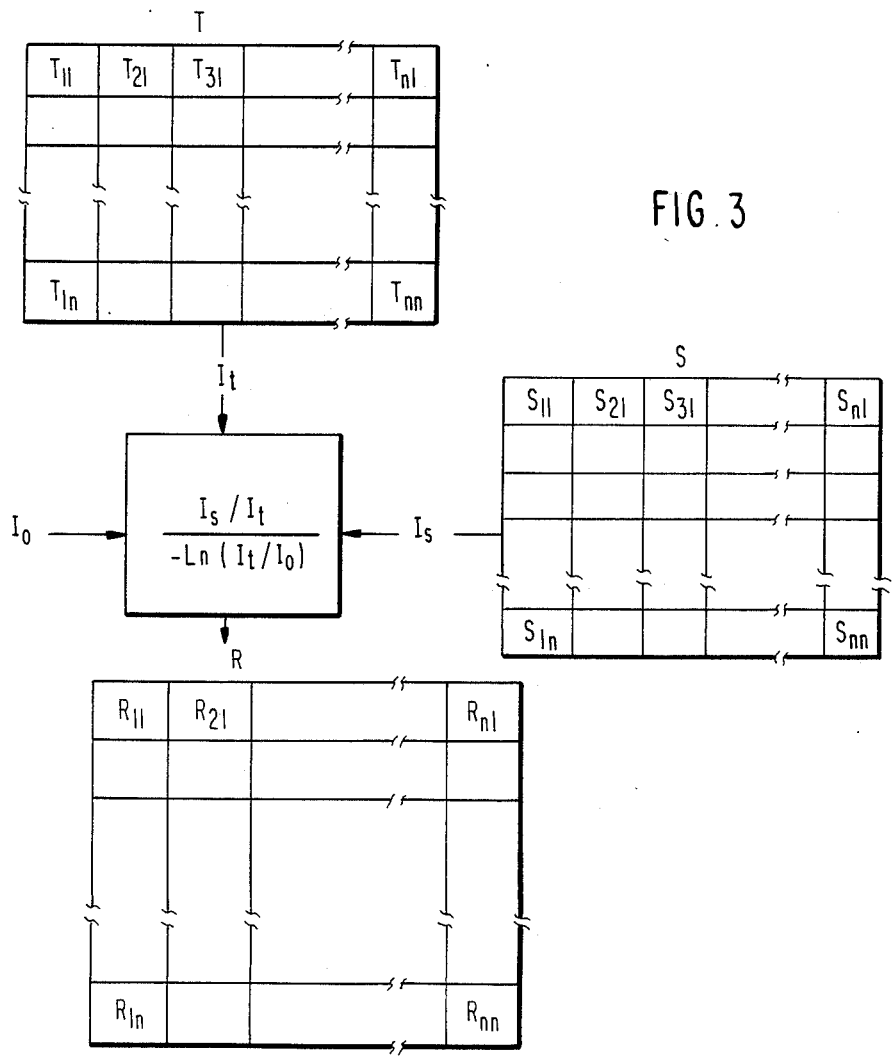
FIG. 3 shows data processing used to develop one type of secondary image.

FIG. 3 schematically shows the processing used to develop the desired or secondary image. FIG. 3 illustrates two arrays, T and S; representative of at least a portion of the read/write memory area of a processor which is subjected to inputs from the first and second detectors. Each of those inputs are sampled and digitized, the inputs from the first detector fills array T and the input from the second detector fills the array S. Those skilled in the art will be aware that there is a one-to-one correspondence between any arbitrary element in array T and the output of the first detector at some instant in time during the period during which the target is being scanned. Likewise, there is a similar correspondence between an element in array S, and the output of the second detector at a corresponding time during the scan of the target O.

Those skilled in the art will realize that each element of each array T, S, is a digitized representation of either the scattered or transmitted intensity reaching one of the detectors 20 or 25 at a particular instant in time. Let us assume for example that T is the array filled with signals derived from detector 20 and S is the array filled with signals derived from detector 25. Since the arrays are filled simultaneously, the same portion of the object O which produced a transmitted ray intensity $T_{1,1}$, produces scattered intensity of $S_{1,1}$, i.e. corresponding positions in each array originate from identical regions in the object O.

FIG. 3 shows that subsequent to filling the arrays, the arrays are combined to produce a further array R. The array R is produced by withdrawing corresponding elements of array T and S and performing the processing directed by equation 27. More particularly, for each element of R, $R_{i,j}$ we compute $$\frac{I_s/I_t}{-\ln(I_t/I_0)},$$

by noting that $I_s = S_{i,j}$; $I_t = T_{i,j}$ and $I_o$ is a constant. Each element in the array R will have a value which is a unique function of the line of sight Z. Thus, the typical radiograph in which image intensity is a mix of density and thickness is replaced by the secondary image R in which intensity is a function of line of sight Z.

To demonstrate the foregoing, a target consisting of wedges of lucite, aluminum and copper of varying thickness was illuminated in accordance with the invention. Both direct and scattered detectors were used and a secondary image was produced in accordance with FIG. 3. FIG. 4 is a plot of intensity vs. atomic number. If the image of FIG. 4 is produced with the window $W_1$, the resulting image will show lucite and the aluminum and copper will be absent. Similarly, with window $W_2$, only aluminum will be apparent and $W_3$ will exclusively show copper. Thus, the composite (copper, aluminum and lucite) target has been selectively imaged by the invention. This plot was developed using copper samples 0.0254 cm and 0.0508 cm thick, lucite samples of thickness 0.9804 and 1.313 cm and four aluminum samples of thickness 0.3175 cm, 0.635 cm, 1.564 cm and 1.247 cm. Note that all the image intensities are clustered at the same R value for each value of Z, i.e. thickness is no longer a significant image variable.

In the case of copper, thickness variation of 100% showed an almost imperceptible variation in R, again sample thickness is no longer a significant image parameter.

In the case of aluminum, images of the four different samples are somewhat spread in the R parameter (from 0.055 to about 0.07). However, even this spread is significantly less than the actual thickness spread of the samples. At least as important is the separation (in R) of image components related to different Z.

FIG. 4 demonstrates an important characteristic of the invention. Assume for example, that a complex object consisting of lucite, aluminum and copper were imaged and that two arrays were produced corresponding to direct and scattered energy. Processing those arrays as shown in FIG. 3 using a level of approximately 0.13 would result in a secondary image in which the lucite alone was present. A similar effect can obviously be produced for the aluminum and/or copper.

This is a particularly useful technique. For example, consider medical imaging where it is desired to produce an image of only the bloodstream of a patient or a specified portion of a patient. With this technique, for example, iodine can be introduced into the bloodstream, and then primary images T and S produced by illuminating the patient or that portion of the patient as described hereinbefore. The secondary array R is produced and then imaged using as a level the R value corresponding to the atomic number of iodine. As a result, the secondary image will show only those portions of the object in which the atomic number corresponds to iodine. By manipulating the level parameter, of course images can be produced displaying other specified portions of the target O. Since the invention is predicated on the assumption that line of sight Z is substantially constant, there are particular lines of sight which will show superior results as compared to other lines of sight. However, those skilled in the art will be able to appropriately apply the invention after reviewing the description.

As another example, outside the medical field, x-ray projection radiography is often used in examining fine arts to see if multiple images exist on one painting. Using this technique, images can be produced corresponding to various pigments. For example, an image can be created displaying only lead-based pigments, another image can be created displaying only cadmium-based pigments, etc.

Still other processing possibilities allow for the creation of images with still different characteristics. Many of these possibilities will occur to those skilled in the art after reviewing this description.

Figure 5:
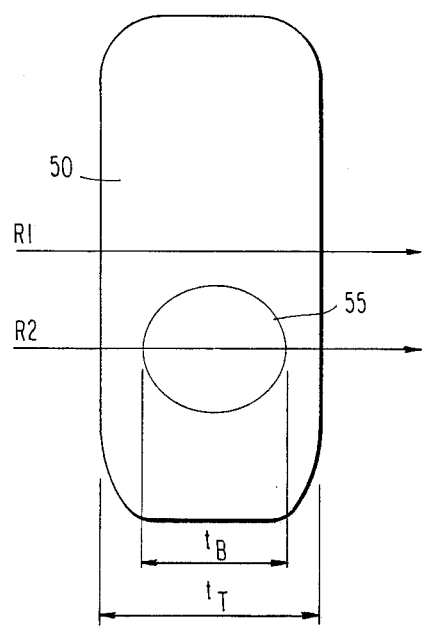
FIG. 5 is a cross-section of a human arm.

As was pointed out hereinabove, the invention can also be applied, beyond producing processed images, to allow calibratable, reproducable measurements of atomic number and density for particular components in a complex object. As an example, FIG. 5 shows a cross-section which is representative of a human arm. The use of the human arm as an example is particularly appropriate since measurements of bone density are desired, but the bone is an internal component, completely submerged in the surrounding muscle and skin. The arm, however, is just an example of a variety of complex objects which include an internal component entirely submerged in another component or components.

For purposes of analysis, the arm cross-section can be considered to consist of two components, flesh and/or muscle tissue 50 within which is located bone tissue 55. As shown in the cross-section of FIG. 5, the total thickness of the arm is $t_T$, whereas the bone 55 which is circular or nearly-circular has a diameter $t_B$. Also shown in FIG. 5 are two representative ray paths, R1 which intercepts only flesh and/or muscle tissue and R2 which intercepts bone tissue as well as flesh and/or muscle tissue.

We begin with (25) and (26), and define:

$$X \equiv I_S/I_t = \int \mu_c \rho \, dy \tag{29}$$

For ray path R1 and all other paths outside the bone tissue 55:

$$X_1 = \int_1 \mu_c \rho \, dy \tag{30}$$

On the other hand, for path R2, and all other paths intercepting the bone tissue 55:

$$X_2 = \int_2 \mu_c \rho \, dy = \int_1 \mu_c \rho \, dy - \frac{t_B}{t_T} \int_1 \mu_c \rho \, dy + \int_B \mu_c \rho \, dy \tag{31}$$

where $\int_2$ is a line of sight integral over path R2 and $\int_B$ is a line integral over a portion of path R2 within the bone tissue 55.

$$X_2 = X_1(1 - t_B/t_T) + \int_B \mu_c \rho \, dy \tag{32}$$

We assume that:

$$\int_B \mu_c \rho \, dy = \mu_{cB} \rho_B t_B \tag{33}$$

which assumes the bone tissue is uniform, a reasonably good assumption, especially as compared to the other tissue 50 within the target O.

We note that:

$$\mu_c \rho \cong Z n \sigma_{KN} \tag{34}$$

where
Z is atomic number
n is atomic density
$\sigma_{KN}$ is the Klein Nishina cross-section for a free electron (a function of energy only)

$$X_2 - X_1(1 - t_B/t_T) = Z_B n_B \sigma_{KN} t_B \tag{35}$$

or $$Z_B n_B = \frac{1}{\sigma_{KN} t_B} [X_2 - X_1(1 - t_B/t_T)] \tag{36}$$

The expression on the left side of equation 36 is a medically significant parameter depending as it does on the mass density of the imaged bone. The ability to sample bone density non-invasively (or remotely) is very significant in determining the necessity for treatment of natural bone degeneration as well as gauging the successful or unsuccessful nature of the treatment. The five quantities on the right side of the equation are $\sigma_{KN}$ (a constant), bone and arm thickness ($t_B$ and $t_T$) which can be accurately measured in a projection radiograph and $X_1$ and $X_2$. The latter are defined in equation 29. With the inventive apparatus, digitized samples of $X_1$ and $X_2$ are derivable from the image arrays T and S. The operator need merely select the regions within which $X_1$ and $X_2$ need to be evaluated, input the other three parameters and the result is a simple arithmetic problem.

Figure 6:
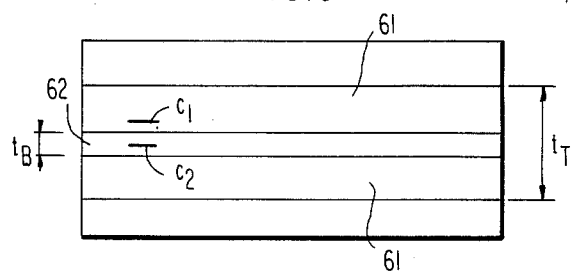
FIG. 6 is a typical projection radiograph of a target such as FIG. 5.
Figure 7:
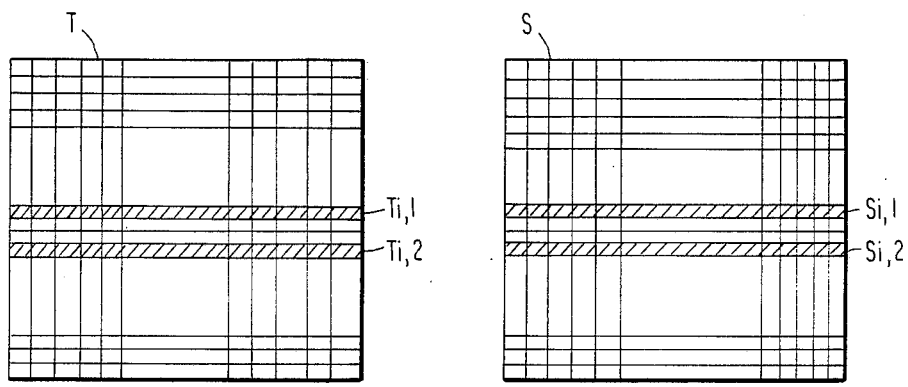
FIG. 7 is illustrations of typical transmitted and scattered image arrays useful in describing an embodiment of the invention.

FIG. 6 is an illustration of a projection radiograph of an arm which could be used to measure $t_T$ and $t_B$; 61 refers to the arm and 62 to the bone. FIG. 7 represents the arrays T and S corresponding to the inventive imaging. Although the illustrations of FIG. 7 only show a partially filled array, this is only for convenience, and in fact each element of arrays T and S has a value corresponding to the sampled and digitized intensity of the transmitted and/or scattered radiation reaching the detector at the particular point in the raster sweep corresponding to the location in the element in the array. The lines of sight for paths R1 and R2 are represented by horizontal lines referenced to a datum, in FIG. 6. By displaying the projection radiograph, the image of FIG. 6 is obtained. The desired lines of sight can be identified by moving a cursor to position $C_1$ (to identify $X_1$) and then to $C_2$ (to identify $X_2$). The cursor positions $C_1$ and $C_2$ correspond to one (or several) pixel high swath(s) through the arrays T and S. $X_1$ and $X_2$ can be directly computed from T and S as a simple ratio. That is, since X is defined as $I_s/I_t$, at any point i,j of either array, $X_{i,j}=S_{i,j}/T_{i,j}$. We need $X_1$ and $X_2$ valid over some length, and for that a mean or average can be computed. This allows numerical solutions to equation 36.

Accordingly, the invention provides for significant improvements in imaging. A preferred embodiment (illustrated in FIGS. 1A, 1B, 2 and 3) provides for acquisition of radiograph data allowing the processing of that data to produce an image which can readily be manipulated to enhance image components based on atomic number, for example as shown in FIG. 4. In another embodiment of the invention, remote measurement of density of a target component is provided for notwithstanding the fact that the component whose density is to be measured may be completely submerged within the target in another component or components.

It should be apparent that many changes can be made within the spirit and scope of the invention, and while the embodiments described herein are representative of the invention, the true scope of the invention is to be determined from the attached claims.

I claim:

1. A projection radiographic apparatus useful in selectively imaging an object using penetrating radiant energy comprising:
    source means for emitting penetrating radiant energy,
    means for directing said penetrating radiant energy emitted by said source means towards a target area including scanning means for producing a flying spot of penetrating radiant energy for repeatedly sweeping a line in space at said target area,
    first radiant energy detecting means located to be responsive to radiant energy from said source means passing directly through an object located in said target area for producing a first sequence of signals as said flying spot sweeps said target area, and
    second radiant energy detecting means located substantially coplanar with said first radiant energy detecting means and further from said source means than said object, said second radiant energy detecting means responsive to radiant energy from said source scattered at an acute angle to a path of said radiant energy from said source means, by an object located in said target area, to produce a second sequence of signals as said flying spot sweeps said target area, said second sequence including only one single valued signal for each signal of said first sequence, and
    combining means for combining said first and second sequences of signals to produce an image array as a nonlinear function of said signals from said first and second sequences.

2. Apparatus as recited in claim 1 in which said combining means includes means for producing an image array with elements of intensity related to atomic number.

3. A projection radiographic apparatus useful in selectively imaging an object using penetrating radiant energy comprising:
    source means for emitting penetrating radiant energy,
    means for directing said penetrating radiant energy emitted by said source means toward a target area including scanning means for producing a flying spot of penetrating radiant energy for repeatedly scanning said target area,
    first radiant energy detecting means located to be responsive to said radiant energy passing directly through an object located in said target area for producing a first signal sequence as said flying spots scan said target,
    second radiant energy detecting means located substantially coplanar with said first radiant energy detecting means and responsive to radiant energy scattered by an object located in said target area for producing a second signal sequence as said flying spot scans said target area, said second sequence including only one single valued signal for each signal in said first sequence of signals,
    combining means for combining said first and second sequences of signals to produce an image array in which said combining means includes:
    means for sampling an output of said first and second radiant energy detecting means for developing first and second sequences of sampled signals;
    means for A to D converting said sequences of sampled signals to produce first and second digital sequences;
    means for storing said first digital sequence in a first ordered array T;
    means for storing said second digital sequence in a second ordered array S; and
    means for processing said first and second ordered arrays for producing a third ordered array R with a single element in said array R corresponding to each element of said first and second digital sequences.

4. Apparatus as recited in claim 3 in which said means for processing includes processing means for computing, for each element of said first and second arrays the quantity:

$$R = \frac{S/T}{-\ln(T/I_o)}$$

wherein S is an element from said second array, T is an element of said first array, $I_o$ is a quantity related to illumination intensity of said source means;
    and means for storing said quantity R as a corresponding element of said third array.

5. A method of projection radiographic imaging producing an image array useful in isolating image components of particular tissues, compounds or elements from other image components comprising:
    providing a radiant energy source and a scanning device for repeatedly sweeping a line in space at a target area;
    providing relative movement, between an object located at said target area and said radiant energy, perpendicular to the sweep of said radiant energy;
    detecting, in a given plane, radiant energy transmitted by said object as said radiant energy source sweeps said target area;

detecting, substantially in said given plane, radiant energy scattered at an acute angle to path of said radiant energy from said source, by said object as said radiant energy source sweeps said target area;

processing said detected radiant energy to produce transmitted and scattered radiant energy signals related respectively to transmitted and scattered radiant energy, wherein said processing step produces only a single scattered radiant energy signal for each transmitted radiant energy signal; and producing result signals as a non-linear function of said radiant energy signals and producing an image array from said result signals.

6. A method as recited in claim 5 in which said processing step includes sampling and A/D conversion and in which said producing step produces an image array with elements of intensity related to atomic number.

7. A method as recited in claim 5 or 6 in which said producing step produces the quantity:

$$R = \frac{S/T}{-\ln(T/I_o)}$$

where T and S are transmitted and scattered radiant energy signals, respectively, $I_o$ is a constant related to intensity of said source and said image array consists of an ordered array of said quantity R.

8. A method as recited in claim 5 in which said producing step produces an image array of elements having intensity related to atomic number.

9. A method of remote measurement of density of a component of a complex target in which said component is entirely submerged in another component of said complex target comprising the steps of:

measuring thickness of a selected section of said complex object and thickness of said component at said section;

illuminating said section of said complex object in at least two swaths with a sweeping beam of radiant energy directed approximately perpendicular to said selected section while slowly indexing said target relative to said sweeping beam so that said first swath has a line of sight excluding said component and said second swath has a line of sight including said component;

simultaneously detecting transmitted and scattered radiant energy from said target;

sampling and storing said detected transmitted and scattered radiant energy in a pair of ordered arrays T and S, respectively, and computing a representation of density as:

$$\frac{[S_{i,b}/T_{i,b} - S_{i,a}/T_{i,a}(1 - t_B/t_T)]}{\sigma_{KN} t_B}$$

where the subscripts, i,b and i,a respectively identify said second and first swaths, $t_B$ identifies said measured component thickness, $t_T$ identifies said measured thickness of said complex object and $\sigma_{KN}$ is the Klein Nishina cross-section for a free electron.

10. Apparatus useful in selectively imaging an object using penetrating radiant energy comprising:

source means for emitting penetrating radiant energy, means for directing said penetrating radiant energy emitted by said source means towards a target area, first radiant energy detecting means located to be responsive to said radiant energy passing directly through an object located in said target area, second radiant energy detecting means located to be responsive to said radiant energy scattered by an object located in said target area, image developing means responsive to signals produced by said first and second radiant energy detecting means, said image developing means includes:

means responsive to said first and second radiant energy detecting means for deriving first and second sequences of signals therefrom, means for storing said first sequence in a first ordered array T;

means for storing said second sequence in a second ordered array S; and means for combining said first and second ordered arrays for producing and storing a third ordered array R, wherein said means for combining includes means for computing, for each element of said first and second arrays the quantity:

$$R = \frac{S/T}{-\ln(T/I_o)}$$

wherein S is an element from said second array, T is an element of said first array, $I_o$ is a quantity related to illumination intensity of said source means.

11. A method of imaging producing an image array useful in isolating image components of particular tissues, compounds or elements from other image components comprising:

providing radiant energy source means for repeatedly sweeping a target with radiant energy;

providing relative movement between said target and said radiant energy perpendicular to the sweep of said radiant energy;

detecting radiant energy transmitted by said target;

detecting radiant energy scattered by said target;

processing said detected radiant energy to produce transmitted and scattered radiant energy signals related respectively to transmitted and scattered radiant energy; and combining said radiant energy signals to produce the quantity:

$$R = \frac{S/T}{-\ln(T/I_o)}$$

where T and S are transmitted and scattered radiant energy signals, respectively, $I_o$ is a constant related to intensity of said source and said image array consists of an ordered array of said quantity R.

12. A method as recited in claim 11 in which said processing step includes sampling and A/D conversion.

13. A method useful in remote measurement of density of a component of a complex object in which said component is entirely submerged in said complex object comprising the steps of:

measuring thickness of a selected section of said complex object and thickness of said component at said selected section;

illuminating said selected section of said complex object in at least two swaths with a sweeping beam of radiant energy directed approximately perpendicular to said selected section while slowly indexing said target relative to said sweeping beam so that a first swath has a line of sight excluding said component and a second swath has a line of sight including said component;

simultaneously and separately detecting transmitted and scattered radiant energy from said target;

sampling and storing signals corresponding to said detected transmitted and scattered radiant energy in a pair of ordered arrays T and S, respectively, computing for said first swath a first ratio of scattered and transmitted radiant energy, computing for said second swath a second ratio of scattered to transmitted radiant energy, and computing, with said first and second ratios, the density, of said component.

14. A method as recited in claim 13 wherein said first ratio is multiplied by a quantity related to the ratio of the measured component thickness and measured thickness of said complex object.

15. The method of claim 13 or 14 in which said simultaneously detecting step is carried out with detectors located in substantially common planes.

16. Projection radiographic apparatus useful in selectively imaging an object located in a target area using penetrating radiant energy comprising:

source means for emitting penetrating radiant energy, means for directing said penetrating radiant energy emitted by said source means towards said target area including scanning means for producing a flying spot of penetrating radiant energy for repeatedly scanning said target area, first radiant energy detecting means located to be responsive to said radiant energy passing directly through an object located in said target area for producing a first sequence of signals as said flying spots scan said target, second radiant energy detecting means located substantially coplanar with said first radiant energy detecting means, further from said source means than said object and responsive to radiant energy scattered at an acute angle to a path of radiant energy from said source means, by an object located in said target area for producing a second sequence of signals as said flying spot scans said target area, said second sequence including only one valued signal for each signal in said first sequence, and combining means responsive to said first and second signals for producing an image array with elements of intensity related to atomic number.

17. Apparatus useful for producing a projection radiograph for selectively imaging an object using penetrating radiant energy comprising:

source means for emitting penetrating radiant energy, means for directing said penetrating radiant energy emitted by said source means toward a target area including scanning means for producing a flying spot of penetrating radiant energy for repeatedly scanning said target area, first radiant energy detecting means for producing first signals and located to be responsive to said radiant energy passing directly through an object located in said target area as said flying spot scans said target area, second radiant energy detecting means for producing second signals and located to be responsive to radiant energy scattered at an acute angle to a path of said penetrating radiant energy by an object located in said target area as said flying spot scans said target area, combining means for combining said first and second signals to produce an image array in which said combining means includes:

means for sampling an output of said first and second radiant energy detecting means for simultaneously developing first and second sequences of sampled signals with a like number of signals in each sequence;

means for A to D converting said sequences of sampled signals to produce first and second digital sequences;

means for storing said first digital sequence in a first ordered array T to produce an array of a given number of elements;

means for storing said second digital sequence in a second ordered array S to produce an array of said given number of elements; and means for processing said first and second ordered arrays for producing a third ordered array R of said given number of elements wherein R is a reflection of said object's atomic number.

18. Apparatus as recited in claim 17 wherein said third ordered array R includes a plurality of elements, each of said elements being a function of a corresponding element in said first and second arrays T and S, respectively.

19. Apparatus as recited in claim 17 which includes means for producing from said array R an image with elements of intensity related to atomic number.

* * * * *